(12) United States Patent
Tsuchiya et al.

(10) Patent No.: US 9,303,198 B2
(45) Date of Patent: Apr. 5, 2016

(54) HYDROFLUOROPROPENE REFRIGERANT COMPOSITION COMPRISING PHTHALATES

(71) Applicant: DAIKIN INDUSTRIES, LTD., Osaka-shi, Osaka (JP)

(72) Inventors: Tatsumi Tsuchiya, Osaka (JP); Takashi Shibanuma, Osaka (JP); Yasufu Yamada, Osaka (JP); Hitomi Kuroki, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/277,385

(22) Filed: May 14, 2014

(65) Prior Publication Data
US 2014/0248706 A1   Sep. 4, 2014

Related U.S. Application Data

(62) Division of application No. 13/203,352, filed as application No. PCT/JP2010/053108 on Feb. 26, 2010, now abandoned.

(30) Foreign Application Priority Data

Feb. 26, 2009 (JP) ................. 2009-044929

(51) Int. Cl.
*C09K 5/04* (2006.01)
*C10M 171/00* (2006.01)
*G01N 33/28* (2006.01)

(52) U.S. Cl.
CPC ............ *C09K 5/045* (2013.01); *C10M 171/008* (2013.01); *G01N 33/2876* (2013.01); *C09K 2205/126* (2013.01); *C10M 2207/283* (2013.01); *C10M 2209/04* (2013.01); *C10M 2209/103* (2013.01); *C10N 2220/302* (2013.01); *C10N 2230/10* (2013.01); *Y10T 436/153333* (2015.01); *Y10T 436/196666* (2015.01)

(58) Field of Classification Search
CPC .......................... C09K 5/045; C09K 2205/126
USPC ........................................................ 252/67
See application file for complete search history.

(56) References Cited

U.S. PATENT DOCUMENTS

| 5,607,912 | A | 3/1997 | Samejima et al. | |
| 2003/0027729 | A1 | 2/2003 | Kaimai et al. | |
| 2006/0243944 | A1* | 11/2006 | Minor et al. | 252/67 |
| 2007/0108403 | A1* | 5/2007 | Sievert et al. | 252/67 |
| 2008/0157023 | A1 | 7/2008 | Samuels et al. | |
| 2009/0314015 | A1* | 12/2009 | Minor et al. | 62/115 |

FOREIGN PATENT DOCUMENTS

| EP | 2 309 205 A1 | 4/2011 |
| JP | 53-012946 A | 2/1978 |
| JP | 58-121237 A | 7/1983 |
| JP | 3-287557 A | 12/1991 |
| JP | 5-209077 A | 8/1993 |
| JP | 08-134481 A | 5/1996 |
| JP | 2001-200285 A | 7/2001 |
| JP | 2008-208261 A | 9/2008 |
| JP | 2009-298918 A | 12/2009 |
| WO | 2008/027511 A1 | 3/2008 |
| WO | 2008/061079 A2 | 5/2008 |
| WO | 2008/153106 A1 | 12/2008 |
| WO | 2009/003165 A1 | 12/2008 |
| WO | 2009/101872 A1 | 8/2009 |
| WO | 2010/098447 A1 | 9/2010 |

OTHER PUBLICATIONS

Extended European Search Report dated Aug. 8, 2014, issued by the European Patent Office in counterpart European application No. 14158809.5.
Communication dated Jun. 29, 2015, issued by the European Patent Office in corresponding European Application No. 10 746 330.9.
Catalogue Handbook of Fine Chemicals, Aldrich, Bornem, p. 1599, Dec. 31, 1992.
Supplementary European Search Report dated Aug. 23, 2013 for EP Patent Application No. 10746330.9.

* cited by examiner

*Primary Examiner* — John Hardee
(74) *Attorney, Agent, or Firm* — Sughrue Mion, PLLC

(57) ABSTRACT

The present invention provides a stabilized refrigerant composition containing a hydrofluoropropene with low global warming potential (GWP) that can remain stable even in the presence of air (oxygen) for a long period of time. More specifically, the present invention provides a refrigerant composition containing a hydrofluoropropene and a stabilizer. The stabilizer is at least one member selected from the group consisting of alkylcatechols, alkoxyphenols, benzoquinones, phenothiazines, and phthalates.

21 Claims, No Drawings

HYDROFLUOROPROPENE REFRIGERANT COMPOSITION COMPRISING PHTHALATES

This is a Divisional of application Ser. No. 13/203,352 filed Aug. 25, 2011, now abandoned which is a national stage of PCT/JP2010/053108 filed Feb. 26, 2010, and claiming priority based on Japanese Patent Application No. 2009-044929 filed Feb. 26, 2009, the contents of all of which are incorporated herein by reference in their entirety.

TECHNICAL FIELD

The present invention relates to a stabilized refrigerant composition containing a hydrofluoropropene with a low global warming potential, such as 2,3,3,3-tetrafluoropropene.

BACKGROUND ART

Chlorofluorohydrocarbons (CFCs) and hydrochlorofluorocarbons (HCFCs) have been used as refrigerants in refrigerating systems and as heating media in heat pumps. Chlorofluorocarbon (CFC) and hydrochlorofluorocarbon (HCFC) alone, or as azeotropic compositions or mixtures thereof, etc., are collectively called Freon or Freons. In recent years, it has been indicated that Freons released into the atmosphere deplete the ozone layer, thereby inflicting a serious adverse influence on the ecosystem, including humans on earth. Accordingly, the use and production of chlorofluorocarbons that pose a high risk of ozone layer depletion have been restricted under international agreements.

More specifically, dichlorodifluoromethane (CFC-12), mainly used as a refrigerant for domestic refrigerators, car air conditioners, turbo freezers, and container freezers, has been replaced by 1,1,1,2-tetrafluoroethane (HFC-134a) in compliance with the above-mentioned regulations.

However, more strict regulations have been implemented. For example, in the EU, two regulations, the "Regulation on Certain Fluorinated Greenhouse Gases," and the "Directive Relating to Emissions of F-Gas from Air Conditioning Systems Fitted to Cars" (F-gas regulations), were announced in June, 2006. According to these regulations, car air conditioners installed in new model vehicles sold on the market after 2011, and those in all vehicles sold after 2017 must be configured to use a refrigerant having a GWP of not more than 150. Because HFC-134a currently used in vehicles has a GWP of 1,300, $CO_2$, etc., have been proposed as potential replacements for HFC-134a. However, such a replacement entails various problems, such as required equipment modification and insufficient refrigeration capacity at high temperatures due to $CO_2$ being a critical fluid. In addition, isobutane (i-$C_4H_{10}$), etc., which have been used as refrigerants for certain types of electric refrigerators, have not been used as replacements in all technical fields due to their very high combustibility.

In view of the above problem, there is a desire to develop a refrigerant with low GWP, which achieves performance equivalent to or better than HFC-134a in terms of energy efficiency, refrigerant characteristics (e.g., refrigeration capacity, boiling point, and pressure), etc., in LCCP (Life Cycle Climate Performance) evaluation; and which requires no or only slight modification of equipment.

In this regard, hydrofluoropropenes such as 1,2,3,3,3-pentafluoro-1-propene (HFO-1225ye) and 2,3,3,3-tetrafluoro-1-propene (HFO-1234yf) are known as low GWP compounds having an unsaturated bond in the molecule. These compounds, which have a GWP lower than saturated HFC compounds, were expected to be less stable in the atmosphere than saturated HFC compounds.

The present inventors evaluated the stability of such hydrofluoropropenes, and found stability problems relating to hydrofluoropropenes in the presence of air (oxygen). More specifically, the evaluation results confirmed that progressive oxidative degradation occurred even in the temperature range to which refrigerant compositions may be exposed during actual use, thus forming acids such as $CF_3COOH$ and HF. Therefore, problems such as system corrosion, reduction of refrigeration capacity, capillary blockage, etc., were expected to occur.

In general, in mobile air conditioners or like devices to which a refrigerant is charged at the factory under construction management, there is little possibility of an air (oxygen) entrapment problem. However, stationary air conditioners or like devices are required to be charged with a refrigerant on site. The charging of the refrigerant relies on the contractor's management ability. Thus, entrapped air (oxygen) has been considered to be a primary cause of failures and problems, such as reduction of refrigeration capacity.

In conventional HFC refrigerants, replacement of such refrigerants can solve such a problem. However, in hydrofluoropropene-containing refrigerants, oxidative degradation of such refrigerants generates a large amount of acid, which may corrode metal parts of the system, etc., and thus necessitate equipment replacement. Accordingly, problems in installation, maintenance, etc., may occur with the use of hydrofluoropropene-containing refrigerants. Therefore, to use a hydrofluoropropene as a component of refrigerant compositions, a technique for enhancing the stability of the refrigerant compositions in the presence of air (oxygen) is necessary.

For example, as a stabilization technique, Patent Literature (PTL) 1 discloses that a stabilizer such as a phenolic compound, thiophosphate, benzoquinone, or aryl alkyl ether is added to a fluoroolefin.

CITATION LIST

Patent Literature

PTL 1: WO 2008/027511

SUMMARY OF INVENTION

Technical Problem

An object of the present invention is to provide a stabilized refrigerant composition containing a hydrofluoropropene with a low global warming potential (GWP), the refrigerant composition being able to maintain a stable state for a long period of time, even in the presence of air (oxygen).

Solution to Problem

To achieve the above objects, the present inventors carried out extensive research. As a result, the inventors found that a refrigerant composition comprising at least one hydrofluoropropene and at least one stabilizer (an antioxidant) selected from the group consisting of alkylcatechols, alkoxyphenols, benzoquinones, phenothiazines, and phthalates can remain stable even in the presence of air (oxygen) for a long period of time. Such a refrigerant composition can maintain a stable state over a long period of time, even when charged with entrapped air (oxygen) into stationary air conditioners, such as domestic air conditioners.

A principal mechanism of decomposition of conventional HFC refrigerants not containing unsaturated bonds is reduction of a halogen atom. The durable stability of such refrigerants is evaluated, for example, by tests that take into account decomposition-promoting factors, such as temperature, metal (catalyst), water content, and air. On the other hand, the stability of hydrofluoropropenes is evaluated, for example, in Patent Literature (PTL) 1, by a test method comprising heating a mixture of a lubricant and a refrigerant (HFO-1225ye) in the presence of air and a metal catalyst (Fe, Cu, or Al) at 175° C. for 2 weeks, and then evaluating the appearance of the mixture. That is, the stability of hydrofluoropropenes is evaluated by the same accelerated thermal stability test as for conventional refrigerants (HFC refrigerants).

However, this method can only evaluate the appearance of such a mixture in a liquid phase (coloring grade; rating). No sufficient evaluation of refrigerants containing a hydrofluoropropane has been made in terms of generation of acids that cause corrosion in the system and low refrigeration capacity.

The inventors of the present invention revealed that the oxidation reaction between an unsaturated bond of a hydrofluoropropene and oxygen is a primary mechanism of decomposition of a hydrofluoropropene-containing refrigerant, and the oxidation reaction generates acids such as $CF_3COOH$ and HF, which are a principal cause of the above-mentioned problems. The present inventors thus established a method for evaluating the generation of acids. More specifically, the method comprises heat-treating a hydrofluoropropene-containing refrigerant composition at a predetermined temperature for a predetermined time, and then evaluating the acid content of the heat-treated refrigerant composition, or the total acid value of lubricant that may be contained in the heat-treated refrigerant composition. This method enables more practical evaluation of thermal stability of hydrofluoropropene.

The present invention has been accomplished as a result of further research based on the above finding.

More specifically, the present invention provides the following refrigerant compositions containing a hydrofluoropropene.

1. A refrigerant composition comprising a hydrofluoropropene and a stabilizer, the stabilizer being at least one member selected from the group consisting of alkylcatechols, alkoxyphenols, benzoquinones, phenothiazines, and phthalates.
2. The refrigerant composition according to item 1 wherein the hydrofluoropropene is at least one member selected from the group consisting of 2,3,3,3-tetrafluoropropene (HFO-1234yf), (Z- or E-)1,3,3,3-tetrafluoropropene (HFO-1234ze), (Z- or E-)1,2,3,3,3-pentafluoropropene (HFO-1225ye), 1,1,3,3,3-pentafluoropropene (HFO-1225zc), and 3,3,3-trifluoropropene (HFO-1243zf).
3. The refrigerant composition according to item 1 comprising the stabilizer in an amount of 0.1 to 5.0 parts by weight per 100 parts by weight of the hydrofluoropropene.
4. The refrigerant composition according to item 1 further comprising a lubricant.
5. The refrigerant composition according to item 4 wherein the lubricant comprises at least one member selected from the group consisting of polyalkylene glycols, polyol esters, and polyvinyl ethers, and has a kinematic viscosity at 40° C. of 5 to 400 cSt.
6. The refrigerant composition according to any one of items 1 to 5 wherein the refrigerant composition is used for at least one member selected from the group consisting of refrigeration systems, refrigerators, mobile air conditioners, coolers (chillers), container freezers, domestic air conditioners, air conditioners for business use, and vapor compression heat pumps such as hot-water supply systems.
7. A method for stabilizing a refrigerant composition comprising a hydrofluoropropene, the method comprising adding to the refrigerant composition at least one stabilizer selected from the group consisting of alkylcatechols, alkoxyphenols, benzoquinones, phenothiazines, and phthalates.
8. A method for evaluating a refrigerant composition containing a hydrofluoropropene and a stabilizer, the method comprising heat-treating the refrigerant composition in the presence or absence of oxygen in an airtight container, and determining the acid content of the refrigerant composition after the treatment.
9. A method for evaluating a refrigerant composition containing hydrofluoropropene, a lubricant, and a stabilizer, the method comprising heat-treating the refrigerant composition in the presence or absence of oxygen in an airtight container, and then determining the acid content of the refrigerant composition, and/or the total acid value of the lubricant contained in the heat-treated refrigerant composition.

Advantageous Effects of Invention

The refrigerant composition of the present invention is chlorine-free and bromine-free; therefore, the composition has no risk of depleting the ozone layer when released into the atmosphere. Further, the refrigerant composition of the invention has a low global warming potential, and its stability in the presence of air (oxygen) is equivalent to that of known HFC refrigerants. Furthermore, the refrigerant composition of the invention exhibits sufficient durability, even when used for stationary refrigeration systems.

A feature of the refrigerant composition of the present invention is that the composition comprises a hydrofluoropropene and a stabilizer, and that the stabilizer is at least one member selected from the group consisting of alkylcatechols, alkoxyphenols, benzoquinones, phenothiazines, and phthalates.

Examples of hydrofluoropropenes usable as refrigerants include 2,3,3,3-tetrafluoropropene (HFO-1234yf), (Z- or E-)1,3,3,3-tetrafluoropropene (HFO-1234ze), (Z- or E-)1,2,3,3,3-pentafluoropropene (HFO-1225ye), 1,1,3,3,3-pentafluoropropene (HFO-1225zc), 3,3,3-trifluoropropene (HFO-1243zf), and the like. Such hydrofluoropropenes can be used singly, or in a mixture of two or more.

The refrigerant composition of the present invention may contain a known HFC refrigerant, in addition to a hydrofluoropropene as mentioned above.

The HFC refrigerant content is 50 wt % or less, preferably 30 wt % or less, and more preferably 20 wt % or less, based on the total weight of the refrigerant composition.

The refrigerant composition of the present invention may contain, in addition to such a hydrofluoropropene, a lubricant according to the purpose of use. The lubricant may be a known lubricant. Examples thereof include poly(oxy)alkylene glycols, polyvinyl ethers; polyphenylethers, poly(oxy)alkylene glycols, copolymers of a poly(oxy)alkylene glycol monoether and a polyvinyl ether; polyol esters, polycarbonates, silicone, polysiloxane, perfluoroethers, mineral oils, olefin polymers, alkyldiphenylalkanes, alkylnaphthalenes, alkylbenzenes, and the like. Among such lubricants, at least one member selected from the group consisting of poly(oxy)alkylene glycols, polyvinyl ethers, and polyol esters is particularly preferable.

Such lubricants can be used singly, or in a mixture of two or more. The lubricant has a kinematic viscosity at 40° C. of preferably 5 to 400 cSt, and more preferably 30 to 400 cSt. The kinematic viscosity as used herein refers to a value determined by a capillary viscometer among viscometers defined in JIS Z 8803 (a liquid viscosity-measurement method).

When a lubricant is used, the amount of the hydrofluoropropene-containing refrigerant is typically 16 to 50 parts by weight, per 10 parts by weight of the lubricant. However, the amount of the hydrofluoropropene-containing refrigerant is not particularly limited to this range, and may vary depending on the specifications of the oil tank of the refrigeration system.

To impart stability against oxygen to a hydrofluoropropene-containing refrigerant, the refrigerant composition of the present invention contains at least one stabilizer (antioxidant) selected from the group consisting of alkylcatechols, alkoxyphenols, benzoquinones, phenothiazines, and phthalates.

Examples of alkylcatechols include pyrocatechol compounds represented by Formula (1):

[Chem 1]

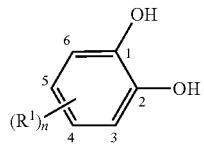

(1)

(wherein $R^1$ is alkyl, and n is an integer of 1 to 4).

Examples of alkyl groups represented by $R^1$ include $C_1$ to $C_{10}$ linear, branched, or cyclic alkyl groups. Specific examples thereof include methyl, ethyl, propyl, isopropyl, n-butyl, isobutyl, sec-butyl, tert-butyl, pentyl, hexyl, cyclopropyl, cyclobutyl, cyclopentyl, and cyclohexyl. Tert-butyl is preferable.

n is preferably 1 or 2, and is more preferably 1. When n is an integer of 2 to 4, the groups represented by $R^1$ may be the same or different. Although $R^1$ may be bonded to any position on the benzene ring, $R^1$ is preferably bonded to the 4- or 5-position.

A preferable example of alkylcatechol is 4-tert-butylpyrocatechol.

Examples of alkoxyphenols include phenolic compounds represented by formula (2):

[Chem 2]

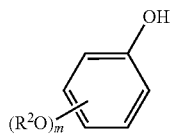

(2)

(wherein $R^2$ is an alkyl group, and m is an integer of 1 to 5).

Examples of the alkyl group represented by $R^2$ include $C_1$ to $C_{10}$ linear, branched, or cyclic alkyl groups. Specific examples thereof include methyl, ethyl, propyl, isopropyl, n-butyl, isobutyl, sec-butyl, and tert-butyl. Methyl, ethyl, isopropyl, and tert-butyl are preferable. m is preferably 1 or 2, and more preferably 1. When n is an integer of 2 to 4, the groups represented by $R^2O$ may be the same or different. Although $R^2O$ may be bonded to any position on the benzene ring, $R^2O$ is preferably bonded to the p-position (4-position).

A preferable example of alkoxyphenol is 4-methoxyphenol.

Examples of benzoquinones include quinone compounds represented by Formula (3):

[Chem 3]

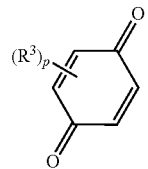

(3)

(wherein $R^3$ is an alkyl group, and p is an integer of 1 to 4).

Examples of alkyl groups represented by $R^3$ include $C_1$ to $C_{10}$ linear, branched, or cyclic alkyl groups. Specific examples thereof include methyl, ethyl, propyl, isopropyl, n-butyl, isobutyl, sec-butyl, and tert-butyl. Methyl, ethyl, isopropyl, and tert-butyl are preferable.

p is preferably 0, 1, or 2, and more preferably 0. When n is an integer of 2 to 4, groups represented by $R^3$ may be the same or different. $R^3$ may be bonded to any position on the ring.

A preferable example of benzoquinone is 1,4-benzoquinone.

Examples of phenothiazines include phenothiazine compounds represented by Formula (4):

[Chem 4]

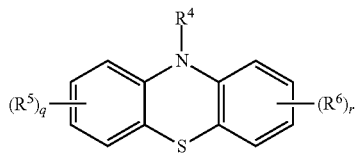

(4)

(wherein $R^4$ is a hydrogen atom or an alkyl group, the groups represented by $R^5$ or the groups represented by $R^6$ may be the same or different, and each represents a hydrogen atom or an alkyl group, q and r may be the same or different, and each represents an integer of 1 to 4).

Examples of alkyl groups represented by $R^4$ include $C_1$ to $C_{10}$ linear, branched, or cyclic alkyl groups. Specific examples thereof include methyl, ethyl, propyl, isopropyl, n-butyl, isobutyl, sec-butyl, and tert-butyl. Methyl, ethyl, isopropyl, and tert-butyl are preferable. $R^4$ is preferably a hydrogen atom.

Alkyl groups represented by $R^5$ and $R^6$ can be suitably selected from those represented by $R^4$. Preferably, both $R^5$ and $R^6$ are hydrogen atoms.

q, and r are preferably 0, 1, or 2, and more preferably 0. When q is an integer of 2 to 4, the groups represented by $R^5$ may be the same or different. When r is an integer of 2 to 4, the groups represented by $R^6$ may be the same or different. $R^5$ and $R^6$ may be bonded to any position on the ring.

A preferable example of phenothiazine is a phenothiazine.

Examples of phthalates include mono- or di-alkali metal salts of phthalic acid. Mono-alkali metal salts of phthalic acid are preferable. Specific examples thereof include potassium hydrogen phthalate and sodium hydrogen phthalate. Potassium hydrogen phthalate is preferable.

The amount of the stabilizer is typically 0.1 to 5.0 parts by weight, and preferably 0.3 to 3.0 parts by weight, per 100 parts by weight of hydrofluoropropene.

An excessively low stabilizer content relative to hydrofluoropropene fails to provide its sufficient effects, whereas an excessively high stabilizer content causes sludge formation, and is undesirable in view of economy. Accordingly, use of the stabilizer in an amount within the above-mentioned range is preferable.

When the stabilizer is poorly soluble in the lubricant, a suitable solvent may be added, insofar as it does not adversely affect the stability of the hydrofluoropropene against oxygen. Examples of usable solvents include glyme compounds. Diglyme is preferable. The amount of the solvent used is 30 wt % or less, preferably 15 to 25 wt %, and more preferably 15 to 20 wt %, based on the total weight of the stabilizer.

The stabilizer used in the present invention exhibits an extremely high stabilization (antioxidation) effect, compared to the stabilizers exemplified in PTL 1 (see the Examples and Comparative Examples).

This is because the stability evaluation method disclosed in PTL 1 only evaluates the appearance (coloring grade; rating) of the mixture in a liquid phase; and cannot evaluate the generation of acids that is a principal cause of corrosion in the system, and reduction of refrigeration capacity.

In contrast, the stability evaluation method according to the present invention comprises heat-treating a refrigerant composition in the presence or absence of oxygen in an airtight container, and then analyzing the acid content of the heat-treated refrigerant composition. When the refrigerant composition contains a lubricant, the method of the present invention further comprises analyzing the total acid value of the lubricant contained in the heat-treated refrigerant composition.

The stabilizer's effect and the effect level can be reliably evaluated by comparing the analysis results obtained in the absence of oxygen (confirming no acid generation in the absence of oxygen) with those obtained in the presence of oxygen.

Examples of airtight containers that can be used include sealed tubes (for example, sealed Pyrex (registered trademark) glass tubes). The evaluation method according to the present invention corresponds to so-called accelerated tests. Accordingly, the heating temperature can be selected, for example, from the range of 90 to 200° C. The heat-treatment time can be selected from the range of 72 to 720 hours. The acid content analysis of the heat-treated refrigerant composition, and the total acid value analysis of the lubricant contained in the oil-containing refrigerant composition can be made by the methods described in the Examples below.

The evaluation method according to the present invention can properly evaluate the generation of acids produced by the oxidation reaction, such as $CF_3COOH$ and $HF$, which are a principal cause of corrosion in the system and reduction of refrigeration capacity. Accordingly, the evaluation method of the invention enables more practical screening of stabilizers.

When high thermal stability is required, a thermal stabilizer for lubricants, or HFC refrigerants used in conventional HFC refrigerant systems, as disclosed, for example, in Japanese Unexamined Patent Publications Nos. 2000-178543 and 2008-308610, and Japanese Patent No. 2863159, may be used together.

Examples of such a thermal stabilizer include (i) aliphatic nitro compounds such as nitromethane, nitroethane, and nitropropane; aromatic nitro compounds such as nitrobenzene and nitrostyrene; aromatic unsaturated fatty compounds such as p-isopropenyltoluene and diisopropenylbenzene; (ii) phenols such as 2,6-di-t-butyl-p-cresol; epoxies such as 1,2-butylene oxide; and amines such as phenyl-α-naphthylamine.

The thermal stabilizer may be one or more compounds selected from the above compounds (i) and (ii). In this case, two or more compounds may be selected from either of the compounds (i) or (ii).

The amount of the thermal stabilizer may vary depending on the type of thermal stabilizer used, insofar as it is selected within a range in which the refrigerant performance is not adversely affected. The refrigerant composition typically contains the thermal stabilizer in an amount of about 0.1 to 5 wt %, and more preferably about 0.3 to 0.3 wt %.

The refrigerant composition of the present invention can be used in the same manner as conventional Freons for various purposes, such as refrigerants, heat transfer media, working fluids, and foaming agents. For example, the refrigerant composition of the invention can be used for freezers, refrigerators, mobile air conditioners, coolers (chillers), container freezers, domestic air conditioners, air conditioners for business use, hot-water supply systems, and like vapor compression heat pumps, and various other low temperature machines. The refrigerant composition of the invention is particularly useful for stationary air conditioners, etc., that are required to be charged with a refrigerant on site, thus resulting in high possibility of entrapped oxygen.

EXAMPLES

The present invention is described below in more detail with reference to Examples and Comparative Examples.

Examples 1 to 13 and Comparative Examples 1 to 22

Preparation of Refrigerant Compositions

The following compounds were prepared as refrigerants.
X: HFO-1234yf ($CF_3CF=CH_2$; produced by Daikin Industries, Ltd.)
Y (Comparative product): HFC-32 ($CF_2H_2$, produced by Daikin Industries, Ltd.)
Z: HFO-1225ye ($CF_3CH=CF_2$, produced by Daikin Industries, Ltd.)

The following compounds were prepared as stabilizers.
A (Comparative product): Ethyl mercaptan
B (Comparative product): 2-Hydroxy-4-methoxybenzophenone
C: 1,4-Benzoquinone
D: Phenothiazine
E: 4-t-Butylpyrocatechol
F: 4-Methoxyphenol
G: Potassium hydroxide phthalate
H: (Comparative product, solvent alone): Diglyme
I: (Comparative product): A mixture of 2-hydroxy-4-methoxybenzophenone (2.5 parts by weight)+diglyme (0.5 parts by weight)
J: A mixture of 1,4-benzoquinone (2.5 parts by weight)+diglyme (0.5 part by weight)
K: A mixture of phenothiazine (2.5 parts by weight)+diglyme (0.5 part by weight)
L: A mixture of 4-t-butylpyrocatechol (2.5 parts by weight)+diglyme (0.5 parts by weight)
M: A mixture of 4-methoxyphenol (2.5 parts by weight)+diglyme (0.5 parts by weight)

A lubricant mainly consisting of a polyvinyl ether compound having a constitutional unit represented by Formula (i) below and having a kinematic viscosity at 40° C. of about 70 $mm^2/s$ was prepared as the lubricant.

[Chem 5]

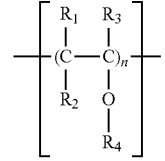

Formula (i)

Refrigerant compositions having the formulations shown below in Tables 1 and 2 were prepared.

TABLE 1

| | Refrigerant | | | Stabilizer | | | | | | | | | | | | | Lubricant | Oxygen concentration relative to the refrigerant mol % (post-adjustment) |
|---|---|---|---|---|---|---|---|---|---|---|---|---|---|---|---|---|---|---|
| | X | Y | Z | A | B | C | D | E | F | G | H | I | J | K | L | M | | |
| Com. Ex. 1 | 100 | | | | | | | | | | | | | | | | 0 | 0 |
| Com. Ex. 2 | | 100 | | | | | | | | | | | | | | | 0 | 0 |
| Com. Ex. 3 | | | 100 | | | | | | | | | | | | | | 0 | 0 |
| Com. Ex. 4 | 100 | | | | | | | | | | | | | | | | 0 | 0.185 |
| Com. Ex. 5 | | 100 | | | | | | | | | | | | | | | 0 | 0.185 |
| Com. Ex. 6 | | | 100 | | | | | | | | | | | | | | 0 | 0.185 |
| Com. Ex. 7 | 74 | 18 | | | | | | | | | | | | | | | 0 | 0.137 |
| Com. Ex. 8 | | | 100 | 3 | | | | | | | | | | | | | 0 | 0.185 |
| Com. Ex. 9 | 100 | | | 3 | | | | | | | | | | | | | 0 | 0.185 |
| Com. Ex. 10 | 100 | | | | 3 | | | | | | | | | | | | 0 | 0.185 |
| Com. Ex. 11 | | | | | | | | | | | | | | | | | 100 | 0 |
| Com. Ex. 12 | | | | | | | | | | | | | | | | | 100 | 0.185 |
| Com. Ex. 13 | 100 | | | | | | | | | | | | | | | | 100 | 0 |
| Com. Ex. 14 | | 100 | | | | | | | | | | | | | | | 100 | 0 |
| Com. Ex. 15 | | | 100 | | | | | | | | | | | | | | 100 | 0 |
| Com. Ex. 16 | 100 | | | | | | | | | | | | | | | | 100 | 0.185 |
| Com. Ex. 17 | | 100 | | | | | | | | | | | | | | | 100 | 0.185 |
| Com. Ex. 18 | | | 100 | | | | | | | | | | | | | | 100 | 0.185 |
| Com. Ex. 19 | 100 | | | 3 | | | | | | | | | | | | | 100 | 0.185 |
| Com. Ex. 20 | | | 100 | 3 | | | | | | | | | | | | | 100 | 0.185 |
| Com. Ex. 21 | 100 | | | | 3 | | | | | | | | | | | | 100 | 0.185 |
| Com. Ex. 22 | 100 | | | | | | | | | 3 | | | | | | | 100 | 0.185 |
| Com. Ex. 23 | 100 | | | | | | | | | | 0.5 | | | | | | 100 | 0.185 |
| Com. Ex. 24 | 74 | 18 | | | | | | | | | | | | | | | 92 | 0.137 |

(In Table 1, the numerical values are parts by weight, unless otherwise specified. In Comparative Example 12, the amount of oxygen was the same as in Comparative Example 4.)

TABLE 2

| | Refrigerant | | | Stabilizer | | | | | | | | | | | | | Lubricant | Oxygen concentration relative to the refrigerant mol % (post-adjustment) |
|---|---|---|---|---|---|---|---|---|---|---|---|---|---|---|---|---|---|---|
| | X | Y | Z | A | B | C | D | E | F | G | H | I | J | K | L | M | | |
| Ex. 1 | 100 | | | | 3 | | | | | | | | | | | | 100 | 0.185 |
| Ex. 2 | | 100 | | | | | | | | | | | | 3 | | | 100 | 0.185 |
| Ex. 3 | 100 | | | | | 3 | | | | | | | | | | | 100 | 0.185 |
| Ex. 4 | 100 | | | | | | 3 | | | | | | | | | | 100 | 0.185 |
| Ex. 5 | 100 | | | | | | | 3 | | | | | | | | | 100 | 0.185 |
| Ex. 6 | 100 | | | | | | | | 3 | | | | | | | | 100 | 0.185 |

TABLE 2-continued

| | Refrigerant | | | Stabilizer | | | | | | | | | | | | | Lubricant | Oxygen concentration relative to the refrigerant mol % (post-adjustment) |
|---|---|---|---|---|---|---|---|---|---|---|---|---|---|---|---|---|---|---|
| | X | Y | Z | A | B | C | D | E | F | G | H | I | J | K | L | M | | |
| Ex. 7 | 100 | | | | | | | | | | | | 3 | | | | 100 | 0.185 |
| Ex. 8 | 100 | | | | | | | | | | | | | 3 | | | 100 | 0.185 |
| Ex. 9 | 100 | | | | | | | | | | | | | | 3 | | 100 | 0.185 |
| Ex 10 | 100 | | | | | | | | | | | | | | | 3 | 100 | 0.185 |
| Ex 11 | 74 | 18 | | | | | | | | | | | | | 2.8 | | 92 | 0.185 |
| Ex.12 | 100 | | | | | | | | | | | | | | 3 | | 0 | 0.185 |
| Ex 13 | | | 100 | | | | | | | | | | | | 3 | | 0 | 0.185 |

(In Table 2, the numerical values are parts by weight, unless otherwise specified.)

Test Example 1

A total of 37 kinds (Examples 1 to 13, and Comparative Examples 1 to 24) of refrigerant compositions (a refrigerant+a stabilizer+a lubricant) shown in Table 1 were individually placed into Pyrex (registered trademark) glass tubes (ID 8 mm$\phi$×OD 12 mm$\phi$×L 300 mm). Air was added to each tube to achieve the oxygen concentrations shown in Table 1. After the tubes were sealed, an accelerated test was performed by heating the tubes at 150° C. for 1 week (for 168 hours).

(Acid Content Analysis Method)

After the accelerated test, gas in each sealed tube was completely solidified with liquid nitrogen. The sealed tube was then opened. The gradually defrosted and evaporated gas was collected in a Tedlar bag. Five grams of pure water was added to the Tedlar bag and brought into close contact with the collected gas; afterward, acids were extracted. The extract was subjected to ion chromatography to determine the content (weight ppm) of fluoride ion ($F^-$) and trifluoroacetic acid ion ($CF_3COO^-$).

(Analysis of Total Acid Value of Lubricant)

The total acid value of the lubricant after collection of gas was determined according to the total acid value analysis method (for lubricant) of JIS K-2211. The lubricant subjected to the accelerated test was weighed and dissolved in a mixed solvent of toluene, isopropanol, and water. The solution was neutralized by titration with 1/100N KOH ethanol solution using α-naphtholbenzein as an indicator. The total acid value (mg·KOH/g) of the lubricant was determined from the titer.

Table 3 below shows the results of Comparative Examples. Table 4 shows the results of Examples.

TABLE 3

| | Acid content of gas (mass ppm, relative to the refrigerant) | | Total acid value of lubricant |
|---|---|---|---|
| | $CF_3COO^-$ | $F^-$ | (mg · KOH/g) |
| Comparative Example 1 | <1 | <1 | |
| Comparative Example 2 | <1 | <1 | |
| Comparative Example 3 | <1 | <1 | |
| Comparative Example 4 | 1850 | 310 | |
| Comparative Example 5 | <1 | <1 | |
| Comparative Example 6 | 1815 | 300 | |
| Comparative Example 7 | 1505 | 245 | |
| Comparative Example 8 | 1830 | 305 | |
| Comparative Example 9 | 1840 | 310 | |
| Comparative Example 10 | 1800 | 295 | |
| Comparative Example 11 | —* | — | 0.070 |
| Comparative Example 12 | — | — | 0.334 |
| Comparative Example 13 | <1 | <1 | 0.072 |
| Comparative Example 14 | <1 | <1 | 0.068 |
| Comparative Example 15 | <1 | <1 | 0.074 |
| Comparative Example 16 | 8 | 3 | 0.550 |
| Comparative Example 17 | <1 | <1 | 0.331 |
| Comparative Example 18 | 10 | 3 | 0.579 |
| Comparative Example 19 | 8 | 3 | 0.564 |
| Comparative Example 20 | 7 | 2 | 0.560 |
| Comparative Example 21 | 7 | 3 | 0.558 |
| Comparative Example 22 | 9 | 2 | 0.510 |
| Comparative Example 23 | 7 | 2 | 0.515 |
| Comparative Example 24 | 6 | 2 | 0.508 |

*No refrigerant

TABLE 4

| | Acid content of gas (mass ppm, relative to the refrigerant) | | Total acid value of lubricant |
|---|---|---|---|
| | $CF_3COO^-$ | $F^-$ | (mg · KOH/g) |
| Example 1 | <1 | <1 | 0.108 |
| Example 2 | <1 | <1 | 0.104 |
| Example 3 | <1 | <1 | 0.111 |
| Example 4 | <1 | <1 | 0.113 |
| Example 5 | <1 | <1 | 0.115 |
| Example 6 | <1 | <1 | 0.112 |
| Example 7 | <1 | <1 | 0.107 |
| Example 8 | <1 | <1 | 0.101 |
| Example 9 | <1 | <1 | 0.104 |
| Example 10 | <1 | <1 | 0.106 |
| Example 11 | <1 | <1 | 0.100 |
| Example 12 | <1 | <1 | |
| Example 13 | <1 | <1 | |

(Results)

In Comparative Examples 1 to 7, 11 to 18, and 24, no stabilizers were used.

The compositions of Comparative Examples 1 to 3 respectively consisted of HFO-1234yf, HFC-32, and HFO-1225ye, and their stability in the absence of oxygen was evaluated. No noticeable signs of decomposition were detected.

The compositions of Comparative Examples 4 to 6 were the same as those of Comparative Examples 1 to 3, respectively, except that oxygen was present therewith. In Comparative Examples 4 and 6 respectively using HFO-1234yf and HFO-1225ye as hydrofluoropanes, generation of largely increased amounts of acids was observed. This result indicates that hydrofluoropropanes are much less stable in the presence of oxygen, compared to a conventional HFC refrigerant (HFC-32).

The amount of acids generated in Comparative Example 7 using a mixture of HFO-1234yf and HFC-32 in the presence of oxygen was approximately 80% that of Comparative Example 4 using HFO-1234yf alone as a refrigerant, which is thus approximately proportional to the composition ratio of HFO-1234yf in the mixture.

In Comparative Examples 8 and 9, ethyl mercaptan disclosed in Patent Literature 1 (WO 2008/027511) was added as stabilizer A. However, the amount of acids generated in Comparative Examples 8 and 9 was almost equivalent to that of Comparative Examples 4 and 6. This result indicates that stabilizer A did not exhibit oxidation inhibitory effects. Stabilizer A (ethyl mercaptan) was also added to lubricant-containing compositions in Comparative Examples 19 and 20. The total acid value in Comparative Examples 19 and 20 was equivalent to that of Comparative Examples 16 and 18, in which no stabilizers were used. This result indicates that ethyl mercaptan does not have oxidation inhibitory effects on HFO-1234yf or HFO-1225ye.

In Comparative Examples 11 and 12, the total acid value of lubricant alone in the presence and in the absence of oxygen was compared. The total acid value was low (0.070 mg·KOH/g) in the absence of oxygen. The total acid value was high (0.334 mg·KOH/g) in the presence of oxygen. The total acid value in the absence of oxygen (Comparative Example 11) was approximately that of Comparative Examples 13 to 15. Thus, the results indicate that the increase in total acid value is attributable to thermal degradation of ether oil with no decomposition of the refrigerant.

The total acid value in the presence of oxygen (Comparative Example 12) was approximately that of Comparative Example 17. This result indicates that the increase in total acid value is attributable to a reaction between ether oil and oxygen. Therefore, the total acid value did not increase when HFC-32 existed in the presence of oxygen. Accordingly, oxidation inhibitory effects of stabilizers on hydrofluoropropenes (e.g., HFC-1234yf) were determined using the results of Comparative Example 17 as a reference.

In Comparative Examples 13 to 15, the compositions containing the same components as in Comparative Examples 1 to 3 and additionally containing lubricant were evaluated. The evaluation results of Comparative Examples 13 to 15 indicate that the stability of HFO-1234yf in the absence of oxygen is equivalent to that of HFC-32 regardless of the presence or absence of lubricant.

In Comparative Example 16, the total acid value of the lubricant increased, but detection level of acids was lower than that of Comparative Example 4, in which lubricant was not used.

This is probably for the following reason. Since the detected acids were HF (19.5° C.) and $CF_3COOH$ (boiling point: 72.4° C.), most of the acids were dissolved in the lubricant, which increased the total acid number of the lubricant.

In Comparative Example 4, the acid content of the lubricant-free composition in the presence of oxygen was 1850 mass ppm of $CF_3COO^-$ and 310 mass ppm of $F^-$. Conversion of these values to total acid value of lubricant would be 1.78 mg·KOH/g, which is about 9 times greater than 0.22 mg·KOH/g, i.e., the difference between the oil total acid value in Comparative Example 17 as a reference and that of Comparative Examples 16 and 18.

This is, for example, because in the presence of the lubricant, contact of HFO-1234yf with oxygen is reduced due to dissolution of the refrigerant in the oil, etc.

In Comparative Example 24, in which a mixture of refrigerants, HFO-1234yf and HFC-32, existed in the presence of the lubricant and oxygen, the oil total acid value (mg·KOH/g) was 0.508. When only HFO-1234yf was used as a refrigerant (Comparative Example 15), the oil total acid value was 0.550, and the oil total acid value due to oxidation of lubricant (Comparative Examples 11 and 16) was 0.331. Thus, the oil total acid value in Comparative Example 24 was approximately 80% of the difference, which is thus approximately proportional to the composition ratio of HFO-1234yf in the mixture, even in the presence of lubricant.

The oil total acid value in Examples 1 to 11 was lower than that of Comparative Example 17. This is probably because the stabilizer having inhibitory effects not only inhibits the formation of acids by a reaction between HFO-1234yf and oxygen, but also inhibits oxidation of ether oil with oxygen.

In Example 2 using HFO-1225ye as a refrigerant, the additive added exhibited inhibitory effects as in Example 9 using HFO-1234ye alone as a refrigerant. The result shows that even when a hydrofluoropropene other than HFO-1234yf is used, the additive can suppress the oil total acid number, thus exhibiting oxidation inhibitory effects.

In Example 11 using a composition containing HFO-1234yf and HFC-32 as a refrigerant, the oil total acid value was suppressed as in Example 9 using HFO-1234yf alone as a refrigerant. This result indicates that the stabilizer exhibits an oxidation inhibitory effect even when the refrigerant is a composition containing HFC.

In Examples 2 and 9, inhibitory effects of stabilizer L on different types of hydrofluoropropenes were compared in the presence of the lubricant. Regardless of the type of hydrofluoropropene, both the acid content and the oil total acid value were suppressed.

In Examples 12 and 13, inhibitory effects of the stabilizer on different types of hydrofluoropropenes were compared in a system not containing the lubricant. The amount of acids generated was suppressed in Example 13 (using HFO-1225ye) as well as in Example 12 (using HFO-1234yf). Thus, the results indicate that the stabilizer can exhibit inhibitory effects, regardless of the type of hydrofluoropropene.

Thus, the results indicate that the stabilizer exhibits inhibitory effects, regardless of the presence or absence of lubricant and type of hydrofluoropropene.

The above results confirmed that when the stabilizer is used, hydrofluoropropenes, such as 2,3,3,3-tetrafluoropropene, and hydrofluoropropene-containing refrigerant compositions, even in the presence of air (oxygen), can exhibit high stability against oxygen, which is equivalent to that of HFC refrigerants. That is, when the stabilizer of the present invention is added to a hydrofluoropropene having an unsaturated bond, the stability of the hydrofluoropropene in the presence of oxygen can be enhanced to a level equivalent to that of HFC refrigerants. It was thus found that the refrigerant composition of the present invention is useful as a refrigerant composition for stationary air conditioners, which is as stable as conventional HFC refrigerants and which exerts very little effect on the global environment.

The invention claimed is:

1. A refrigerant composition comprising a hydrofluoropropene and a stabilizer, wherein the stabilizer comprises mono- or di-alkali metal salts of phthalic acid.

2. The refrigerant composition according to claim 1 wherein the hydrofluoropropene is at least one member selected from the group consisting of 2,3,3,3-tetrafluoropropene (HFO-1234yf), (Z- or E-)1,3,3,3-tetrafluoropropene (HFO-1234ze), (Z- or E-) 1,2,3,3,3-pentafluoropropene (HFO-1225ye), 1,1,3,3,3-pentafluoropropene (HFO-1225zc), and 3,3,3-trifluoropropene (HFO-1243zf).

3. The refrigerant composition according to claim 1 comprising the stabilizer in an amount of 0.1 to 5.0 parts by weight per 100 parts by weight of the hydrofluoropropene.

4. The refrigerant composition according to claim 1 further comprising a lubricant.

5. The refrigerant composition according to claim 4 wherein the lubricant comprises at least one member selected from the group consisting of polyalkylene glycols, polyol esters, and polyvinyl ethers, and has a kinematic viscosity at 40° C. of 5 to 400 cSt.

6. The refrigerant composition according to any one of claims 1 to 5 wherein the refrigerant composition is used for at least one member selected from the group consisting of refrigeration systems, refrigerators, mobile air conditioners, coolers (chillers), container freezers, domestic air conditioners, air conditioners for business use, and vapor compression heat pumps such as hot-water supply systems.

7. The refrigerant composition according to claim 1, wherein the stabilizer comprises mono-alkali metal salts of phthalic acid.

8. The refrigerant composition according to claim 7, wherein the stabilizer comprises potassium hydrogen phthalate.

9. The refrigerant composition according to claim 7, wherein the stabilizer comprises sodium hydrogen phthalate.

10. A method for stabilizing a refrigerant composition containing a hydrofluoropropene, the method comprising adding to the refrigerant composition a stabilizer comprising mono- or di-alkali metal salts of phthalic acid.

11. The method for stabilizing a refrigerant composition containing a hydrofluoropropene according to claim 10, wherein the stabilizer comprises mono-alkali metal salts of phthalic acid.

12. The method for stabilizing a refrigerant composition containing a hydrofluoropropene according to claim 11, wherein the stabilizer comprises potassium hydrogen phthalate.

13. The method for stabilizing a refrigerant composition containing a hydrofluoropropene according to claim 11, wherein the stabilizer comprises sodium hydrogen phthalate.

14. A method for evaluating a refrigerant composition comprising a hydrofluoropropene and a stabilizer comprising mono- or di-alkali metal salts of phthalic acid, the method comprising heat-treating the refrigerant composition in the presence or absence of oxygen in an airtight container, and determining the acid content of the refrigerant composition after the treatment.

15. The method for evaluating a refrigerant composition comprising a hydrofluoropropene and a stabilizer comprising mono- or di-alkali metal salts of phthalic acid according to claim 14, wherein the stabilizer comprises mono-alkali metal salts of phthalic acid.

16. The method for evaluating a refrigerant composition comprising a hydrofluoropropene and a stabilizer comprising mono- or di-alkali metal salts of phthalic acid according to claim 15, wherein the stabilizer comprises potassium hydrogen phthalate.

17. The method for evaluating a refrigerant composition comprising a hydrofluoropropene and a stabilizer comprising mono- or di-alkali metal salts of phthalic acid according to claim 15, wherein the stabilizer comprises sodium hydrogen phthalate.

18. A method for evaluating a refrigerant composition comprising hydrofluoropropene, a lubricant, and a stabilizer comprising mono- or di-alkali metal salts of phthalic acid, the method comprising heat-treating the refrigerant composition in the presence or absence of oxygen in an airtight container, and then determining the acid content of the refrigerant composition, and/or the total acid value of the lubricant contained in the heat-treated refrigerant composition.

19. The method for evaluating a refrigerant composition comprising hydrofluoropropene, a lubricant, and a stabilizer comprising mono- or di-alkali metal salts of phthalic acid according to claim 18, wherein the stabilizer comprises mono-alkali metal salts of phthalic acid.

20. The method for evaluating a refrigerant composition comprising a hydrofluoropropene and a stabilizer comprising mono- or di-alkali metal salts of phthalic acid according to claim 19, wherein the stabilizer comprises potassium hydrogen phthalate.

21. The method for evaluating a refrigerant composition comprising a hydrofluoropropene and a stabilizer comprising mono- or di-alkali metal salts of phthalic acid according to claim 19, wherein the stabilizer comprises sodium hydrogen phthalate.

* * * * *